United States Patent [19]
Ackrell et al.

[11] 4,055,574
[45] Oct. 25, 1977

[54] 6,11-DIHYDRODIBENZO-[B.E.]-THIEPIN-11-ONE-3-THIOACETATES

[75] Inventors: Jack Ackrell, Palo Alto, Calif.; Joseph M. Muchowski, Mexico City, Mexico

[73] Assignee: Syntex (U.S.A.) Inc., Palo Alto, Calif.

[21] Appl. No.: 701,779

[22] Filed: July 1, 1976

[51] Int. Cl.$^2$ ............................................. C07D 337/12
[52] U.S. Cl. ................................. 260/327 B; 424/275; 542/413
[58] Field of Search ............ 260/327 B, 240 R, 455 R

[56] References Cited
U.S. PATENT DOCUMENTS 3,849,466  11/1974  Henrick et al. .................. 260/455 R
3,946,036  3/1976  Cadient .......................... 260/327 B

OTHER PUBLICATIONS

Russell, et al., Synth. Meth. Org. Chem., vol. 26, p. 213, 1972.

Primary Examiner—Cecilia M. S. Jaisle
Attorney, Agent, or Firm—Gerard A. Blaufarb; William B. Walker

[57] ABSTRACT

Novel thioesters of 6,11-dihydrodibenzo-[b.e.]-thiepin-11-one-3-acetic acid, (dl) 2-(6,11-dihydrodibenzo-[b.e.]-thiepin-11-one-3-yl)propionic acid and the individual (d) isomers of the latter, and processes for making the same.

18 Claims, No Drawings

6,11-DIHYDRODIBENZO-[B.E.]-THIEPIN-11-ONE-3-THIOACETATES

This invention relates to novel and useful 6,11-dihydrodibenzo-[b.e.]-thiepin-11-one derivatives, and to processes for the production thereof.

More particularly this invention relates to thioesters of 6,11-dihydrodibenzo-[b.e.]-thiepin-11one-3-acetic acid and 2-(6,11-dihydrodibenzo-[b.e.]-thiepin-11-one-3-yl)propionic acid, represented by the formulas:

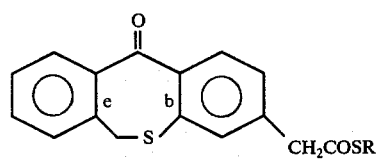
(A)

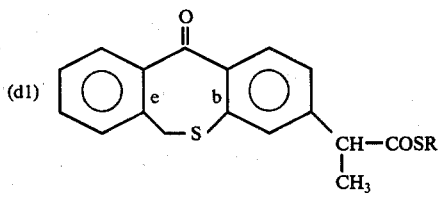
(B)

or the individual (d) isomers of the compounds of Formula (B), wherein R is a lower alkyl group of one to six carbon atoms, phenyl, monosubstituted phenyl, benzyl or mono substituted benzyl.

As used herein, the term "lower alkyl", unless otherwise specified, refers to and includes alkyl groups derived from hydrocarbons of straight or branched chain containing from one to six carbon atoms. Typical lower alkyl groups are methyl, ethyl, propyl, isopropyl, n-butyl, t-butyl, n-pentyl, isoamyl, n-hexyl, isohexyl and the like.

The terms "monosubstituted phenyl" and "monosubstituted benzyl" refer to phenyl and benzyl groups substituted at the o-, m- or p-positions of the aromatic ring by an alkyl group containing from 1 to 4 carbon atoms, e.g., methyl, ethyl, propyl, isopropyl and n-butyl, an alkoxy group containing from 1 to 4 carbon atoms, e.g., methoxy, ethoxy, propoxy, isopropoxy and n-butoxy, chloro, fluoro or bromo.

The compounds of Formulas (A) and (B) and the (d) isomers of Formula (B) are valuable therapeutical agents possessing anti-inflammatory, anagesic and antipyretic activities, also useful as smooth muscle relaxants.

The novel compounds of the present invention can be prepared by treatment of the corresponding acid chloride of the formula

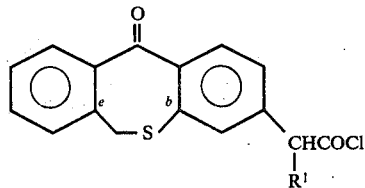
(I)

wherein $R^1$ represents hydrogen or methyl, with a mercaptan of the formula RSH, in which R has the above-indicated meaning.

This reaction is carried out in a suitable anhydrous aprotic solvent, e.g., halogenated hydrocarbons such as methylene chloride, chloroform, carbon tetrachloride and the like, or aromatic hydrocarbons such as benzene, toluene and the like, and it is accelerated in the presence of an acid acceptor, i.e., in the presence of an amine such as pyridine, trimethylamine, triethylamine and the like. The amount of reagents used is not critical, however, it is preferred to use from 1.1 to 2 molar equivalents of both thiol and amine.

This reaction can be effected at a temperature of from 0° to about 40° C, for a period of time sufficient to complete esterification. When the reaction is conducted in the presence of an acid acceptor the desired thioester is readily formed, i.e., the reaction is substantially complete within about one to about 15 minutes, while when no acid acceptor is used the reaction times are of the order of about 16 to about 30 hours.

In the preferred embodiments, the reaction is conducted in methylene chloride solution, at room temperature, using 1.1 to 1.5 molar equivalents of thiol and 1.1 molar equivalents of triethylamine.

Examples of suitable mercaptans are: methyl mercaptan, ethyl mercaptan, propyl mercaptan, n-butyl mercaptan, n-hexyl mercaptan, thiophenol, α-toluenethiol, o-thiocresol, p-methoxythiophenol, p-bromothiophenol, o-chlorothiophenol, p-fluorothiophenol, p-ter-butylthiophenol, o-methylbenzyl mercaptan, p-ethylbenzyl mercaptan, m-methoxybenzyl mercaptan, o-chlorobenzyl mercaptan, m-bromobenzyl mercaptan and p-fluorobenzyl mercaptan. These thiols are known compounds or can be prepared from commercially available precursors.

The acid chlorides of Formula(I) are prepared from the corresponding free acids, which in turn are obtained as described in copending patent application Ser. No. 634,086, filed November 11, 1975, now U.S. Pat. No. 4,000,308, patented Dec. 28, 1976, which is hereby incorporated by reference and made a part hereof, e.g., by treatment with oxalyl chloride or thionyl chloride, by conventional methods, well known in the art.

The thioesters of the present invention can also be prepared from other acid halides, e.g., the bromides, or from the anhydrides of 6,11-dihydrodibenzo-[b.e.]-thiepin-11-one-3-acetic acid, (dl) 2-(6,11-dihydrodibenzo-[b.e.]-thiepin-11-one-3-yl)propionic acid or the individual (d) isomer.

Alternatively, the thioesters of 6,11-dihydrodibenzo-[b.e.]-thiepin-11-one-3-acetic acid can be prepared by a process illustrated by the following reaction sequence:

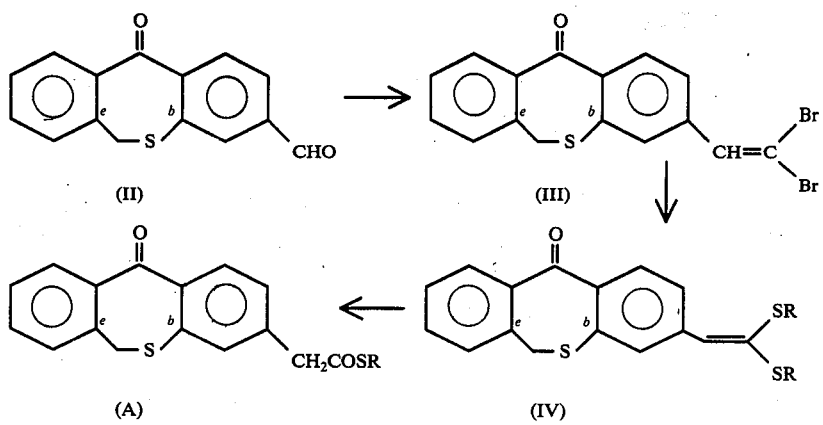

wherein R has the above-indicated meaning.

In practicing the process depicted above, the starting material of Formula (II), i.e. 6,11-dihydrodibenzo-[b.e.]-thiepin-11-one-3-aldehyde, prepared as described in copending application Ser. No. 697,648, filed June 18, 1976, which is hereby incorporated by reference, is treated with a mixture of triphenylphosphine and carbon tetrabromide, to produce the dibromivinyl compound of Formula (III). The reaction is carried out under anhydrous conditions, in a suitable inert organic solvent, e.g., methylene chloride, benzene, toluene, tetrahydrofuran, dimethoxyethane and the like, at a temperature of from about $-10°$ to about $10°$ C for a period of time of from about 30 minutes to about 3 hours.

Treatment of compound (III) with a thiol of the above-indicated type affords the corresponding ketene bisthio-acetal of Formula (IV). The reaction is carried out in the presence of a strong base such as alkali metal hydrides or alkali metal hydroxides, e.g., sodium hydride, potassium hydride, sodium hydroxide, potassium hydroxide and the like, in a suitable inert organic solvent such as dimethylformamide, dimethylacetamide, dimethoxyethane, dimethylsulfoxide and the like, or mixtures thereof at a temperature of from about $-10°$ C to room temperature, for about 30 minutes to about 4 hours. The amount of reagents used is not critical, however, it is preferred to use from 2 to 3 molar equivalents of both thiol and base.

In the preferred embodiments, the reaction is conducted by first reacting the thiol and the base in dimethylformamide as solvent, at about 0° C, adding thereafter a solution of the dibromo compound in the same solvent, maintaining the reaction mixture at 0° C, for about 30 minutes and thereafter at room temperature until completion.

Upon reaction of compound (IV) with trifluoroacetic acid and thereafter with water, at a temperature of from about 0° C to about 40° C, for a period of time of the order of about 16 hours to about 24 hours there is obtained the desired thioester of Formula (A). In the preferred embodiments the reaction is carried out at room temperature contacting initially the starting compound with trifluoroacetic acid, for about 15 to about 30 minutes, treating thereafter the reaction mixture with a small amount of water, and allowing the reaction to proceed for about 18 hours.

The compounds of Formulas (A) and (B), and the (d) acid isomers of Formula (B), are useful as anti-inflammatory agents, analgetic agents, platelet aggregation inhibitors, fibrinolytic agents, and as smooth muscle relaxants. These compounds can be used both prophylactically and therapeutically.

The compounds of Formulas (A) and (B), and the (d) acid isomers of Formula (B), exhibit anti-inflammatory, analgesic and anti-pyretic activities. Accordingly, the compositions containing these compounds are useful in the treatment and elimination of inflammation such as inflammatory conditions of the muscular skeletal system, skeletal joints and other tissues, for example, in the treatment of inflammatory conditions such as rheumatism, concussion, laceration, arthritis, bone fractures, post-traumatic conditions, and gout. In those cases in which the above conditions include pain and pyrexia coupled with inflammation, the instant compounds are useful for the relief of these conditions as well as the inflammation.

Administration of the active compounds of Formulas (A) and (B), and the (d) acid isomers of Formula (B), in an appropriate pharmaceutical composition can be via any of the accepted modes of administration of agents for the treatment of inflammation, pain, or pyrexia, or the prophylaxis thereof. Thus, administration can be for example, orally, parenterally or topically, in the form of solid, semi-solid or liquid dosage forms, such as, for example, tablets, suppositories, pills, capsules, powders, liquids, suspensions, creams, lotions, ointments, or the like, preferably in unit dosage forms suitable for simple administration of precise dosages. The compositions will include a conventional pharmaceutical carrier or excipient and an active compound of Formulas (A) and (B), and the (d) acid isomers of Formula (B), and, in addition, may include other medicinal agents, pharmaceutical agents, carriers, adjuvants, etc.

The preferred manner of administration, for the conditions detailed above, is oral using a convenient daily dosage regimen which can be adjusted according to the degree of affliction. Generally, a daily dose of from 0.05 mg. to 10 mg. of the active compound of Formulas (A) and (B), and the (d) acid isomers of Formula (B), per kilogram of body weight is used. Most conditions respond to treatment comprising a dosage level of the order of 0.25 mg. to 3 mg. per kilogram of body weight per day. For such oral administration, a pharmaceutically acceptable non-toxic composition is formed by the incorporation of any of the normally employed excipients, such as, for example, pharmaceutical grades of mannitol, lactose, starch, magnesium stearate, sodium saccharin, talcum, cellulose, glucose, sucrose, magnesium carbonate and the like. Such compositions take the form of solutions, suspensions, tablets, pills, capsules, powders, sustained release formulations and the like.

The active compounds of Formulas (A) and (B) and the (d) acid isomers of Formula (B) may be formulated into a suppository using, for example, polyalkylene glycols, for example, polypropylene glycol, as the carrier. Liquid pharmaceutically administerable compositions can, for example, be prepared by dissolving, dispersing, etc. an active compound of Formulas (A) and (B) and the (d) acid isomers of Formula (B), and optional pharmaceutical adjuvants in a carrier, such as, for example, water, saline, aqueous dextrose, glycerol, ethanol and the like, to thereby form a solution or suspension. If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

Actual methods of preparing such dosage forms are known, or will be apparent, to those skilled in this art; for example, see Remington's Pharmaceutical Sciences, Mack Publishing Company, Easton, Pennsylvania, 14th. Edition, 1970. The composition to be administered will, in any event, contain a quantity of the active compound(s) in a pharmaceutically effective amount for relief of the particular condition being treated in accordance with the teachings of this invention.

The compounds of Formulas (A) and (B) and the (d) acid isomers of Formula (B) described above are also uterine smooth muscle relaxants and thus are useful as agents for maintaining the pregnancy of pregnant mamals, for the benefit of the mother and/or the fetus, until termination of the pregnancy is considered, from a medical point of view, to be favorable, or more favorable, for the mother and/or the fetus. It should be understood, however, that in certain instances, for example where parturition has already begun (i.e., the mother is experiencing uterine contractions, especially near full term), that administration of the compounds herein described may not maintain the pregnant state for an indefinite period of time. Rather, in such instances, the pregnancy will, most probably, be slightly "prolonged," a factor which may be advantageous to either the mother and/or the fetus.

In particular, the compounds of Formulas (A) and (B), and the (d) acid isomers of Formula (B) are used as agents for delaying the onset of, or for postponing, parturition. As used in this application, the phrase "to delay the onset of parturition" is intended to cover that delay in parturition caused by the administration of the compounds of Formulas (A) and (B), and the (d) acid isomers of Formula (B) at ay time before uterine muscle contractions have begun. Thus, it is intended that the aforementioned phrase cover abortion prevention early in pregnancy (i.e., before the fetus is "viable") as well as delaying premature parturition, a term which sometimes is used with reference to that premature labor experienced later in the pregnancy when the fetus is considered to be "viable." In either case, the agents are administered as prophylactic agents in that such administration tends to prevent the onset of parturition. This administration is particularly useful in the treatment of women having a history of spontaneous abortion, miscarriage or premature delivery (i.e., delivery prior to full term). Such administration is also useful where there are clinical indications that the pregnancy might be terminated prior to that time and is considered favorable to the mother and/or the fetus.

With respect to animals, this treatment can also be utilized to synchronize the deliveries from a group of pregnant animals to happen at or about the same time, or to happen at or about a desired time and/or place, when the births can be handled with greater facility.

As used in this application, the phrase, "postponing parturition" is intended to cover that delay in parturition caused by the administration of the compounds of Formulas (A) and (B), and the (d) acid isomers of Formula (B), after uterine muscle contractions have begun. The condition of the patient, including the time within the gestation period when the contractions have begun, the severity of the contractions and how long the contractions have taken place will affect the results achieved with the administration of the compounds of Formulas (A) and (B), and the (d) acid isomers of Formula (B). For example, the effect can be to reduce the intensity and/or the duration of the contractions (the actual act of parturition being "prolonged"), or to stop the contractions altogether. In either case, the effect will be to prolong the gestation period although, depending upon the condition of the patient as described above, the effect may either be slight or, under appropriate circumstances, somewhat greater. Such administration may be to prevent spontaneous abortion, to cause the delivery to be more easily accomplished and/or less painful to the mother, or to occur at a more appropriate time and/or place.

In all cases, administration of the compounds of Formulas (A) and (B), and the (d) acid isomers of Formula (B) for the purposes set forth herein, should be consistent with best and/or accepted medical (or veterinary) practices so as to maximize the benefits to the mother and the fetus. For example, administration should not be continued so so long past full term that the fetus dies in utero.

In the practice of the methods of the present invention, a therapeutically effective amount of a compound of Formulas (A) and (B), and the (d) acid isomers of Formula (B), or a pharmaceutical composition containing a compound of Formulas (A) and (B), and the (d) acid isomers of Formula (B), is administered to the pregnant mammal via any of the usual and acceptable methods known in the art. The compound can be administered either singly or in combination with another compound or compounds, as defined above, or other pharmaceutical agents, carriers, adjuvants, etc. Such compound(s) or compositions can be administered orally, parenterally, either in the form of solid, semi-solid, or liquid dosage forms. Typically, administration is by a pharmaceutical composition containing the pharmaceutically active compound and one or more pharmaceutical carriers or adjuvants.

The administerable pharmaceutical composition may take the form of oral tablets, vaginal or uterine tablets or suppositories, pills, capsules, liquid solutions, suspensions, or the like, preferably in unit dosage forms suitable for simple administration of precise dosages. Conventional non-toxic solid carriers include, for example, pharmaceutical grades of mannitol, lactose, starch, magnesium stearate, sodium saccharin, talcum, cellulose, glucose, sucrose, magnesium carbonate, and the like. The active compound as defined above may be formulated as suppositories using, for example, polyalkylene glycols, for example, polypropylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine oleate, etc. Actual methods of preparing such dosage forms are known, or will be apparent, to those skilled in this art; for example, see Remington's Pharmaceutical Sciences, Mack Publishing Company, Easton, Penna. 14th Edition, 1970. The composition or formulation to be administered will, in any event, contain a quantity of the active compound(s) in an amount effective to delay the onset of parturition or to postpone parturition if uterine contractions have already begun. Generally a daily dose of from about 5 mg. to about 250 mg. of the active compound per kilogram of body weight will be administered, with administration being a single daily dose or up to three or four smaller doses regularly given throughout the day. The amount of active compound administered will, of course, depend on its relative activity.

The following Preparation and Examples illustrate the invention, but are not intended to limit its scope.

PREPARATION 1

A solution of 300 mg. of 6,11-dihydrodibenzo-[b.e.]-thiepin-11-one-3-acetic acid in 20 ml. of methylene chloride is treated with 0.358 ml. of freshly distilled oxalyl chloride, and the reaction mixture is stirred at room temperature for 18 hours. It is then evaporated to dryness under reduced pressure, and the excess oxalyl chloride is eliminated by repeated benzene distillations (3 × 5 ml.), thus obtaining 338 mg. of crude 6,11-dihydrodibenzo-[b.e.]-thiepin-11-one-3-acetic acid chloride, which is used for the preparation of the thioesters without further purification.

In a similar manner the acid chlorides derived from (dl) 2-(6,11-dihydrodibenzo:[b.e.]-thiepin-11-one-3-yl) propionic acid and (d) 2-(6,11-dihydrodibenzo:[b.e.]-thiepin-11-one-3-yl) propionic acid are prepared from the corresponding free acids.

PREPARATION 2

A. A solution of 50 g. of m-methoxybenzoic acid in 500 ml. of dry tetrahydrofuran is slowly added to a stirred solution of 15 g. of lithium aluminum hydride in 100 ml. of tetrahydrofuran. When the addition is complete the reaction mixture is refluxed for 1 hour, cooled and then treated with 50 ml. of saturated sodium chloride solution. The resultant slurry is filtered and the insoluble material washed with 200 ml. of ether. The combined filtrates are evaporated to dryness to yield an oil which is distilled under reduced pressure, to yield m-methoxybenzyl alcohol as a colourless oil; I.R.: $\nu_{max.}^{film}$ 3630 cm$^{-1}$.

B. A solution of 52 g. of m-methoxybenzyl alcohol in 200 ml. of benzene is treated with 100 ml. of thionyl chloride. The reaction mixture is refluxed for 6 hours, cooled and evaporated under reduced pressure. The residue is taken up in 50 ml. of benzene and the resultant solution is again evaporated under reduced pressure to remove traces of thionyl chloride. The residue is then distilled under reduced pressure to yield 37 g. of m-methoxybenzyl chloride, b.p. 84° C/1.5 mm.

C. A mixture of 5 g. of m-methoxybenzyl chloride, 2 g. of thiourea and 15 ml. of water is stirred for 6 hours at room temperature. The reaction mixture is treated with 3 g. of sodium hydroxide and is then refluxed for 2 hours in a nitrogen atmosphere. The cooled solution is acidified with dilute hydrochloric acid and extracted with ethyl acetate (2 × 10 ml.). The extracts are dried over anhydrous magnesium sulfate and evaporated under reduced pressure, to yield an oil which is distilled under high vacuum, to produce 3 g. of m-methoxybenzyl mercaptan, b.p. 72°–73° C/.05 mm.

In a similar manner, starting from the substituted benzoic acids listed below under I there are obtained the corresponding substituted benzyl mercaptans listed under II.

| I | II |
|---|---|
| o-methylbenzoic acid | o-methylbenzyl mercaptan |
| p-ethylbenzoic acid | p-ethylbenzyl mercaptan |
| o-isopropoxybenzoic acid | o-isopropoxybenzyl mercaptan |
| p-ethoxybenzoic acid | p-ethoxybenzyl mercaptan |
| o-chlorobenzoic acid | o-chlorobenzyl mercaptan |
| m-chlorobenzoic acid | m-chlorobenzyl mercaptan |
| m-bromobenzoic acid | m-bromobenzyl mercaptan |
| p-bromobenzoic acid | p-bromobenzyl mercaptan |
| o-fluorobenzoic acid | o-fluorobenzyl mercaptan |
| p-fluorobenzoic acid | p-fluorobenzyl mercaptan |

EXAMPLE 1

A solution of 0.4 g. of 6,11-dihydrodibenzo-[b.e.]-thiepin-11-one-3-acetic acid chloride (I, R$^1$ =H) in 20 ml. of dry methylene chloride is treated with 0.108 ml. of methyl mercaptan. The reaction mixture is kept at room temperature for 18 hours, 10 ml. of water are then added and the product extracted with methylene chloride (2 × 40 ml.). The combined organic extract is washed with water (2 ×20 ml.), dried over anhydrous sodium sulfate and evaporated to dryness under reduced pressure. Purification of the residue by column chromatography on silica gel (8 g.), using hexane: ethyl acetate (85:15) as eluant, evaporation of the eluate and crystallization of the residue from methylene chloride-hexane affords 332 mg. of S-methyl 6,11-dihydrodibenzo:[b.e.]-thiepin-11-one 3-thioacetate, [(A), R =Me], m.p. 95°–96° C.

EXAMPLE 2

A solution of 300 mg. of 6,11-dihydrodibenzo-[b.e.]-thiepin-11-one-3-acetic acid chloride in 15 ml. of dry methylene chloride is treated with 0.109 ml. of ethyl mercaptan. The reaction mixture is kept at room temperature for 48 hours, following the course of the reaction by t.l.c. on silica gel plates, using hexane:ethyl acetate (70:30) as developing solvent. 10 ml. of water are then added and the product extracted with methylene chloride (2 × 30 ml.). The combined organic extract is washed with water (2 × 15 ml), dried over anhydrous sodium sulfate and evaporated to dryness under reduced pressure. Purification of the oily residue by column chromatography on silica gel (6 g.), using hexane: ethyl acetate (85:15) as eluant, evaporation of the eluate and crystallization of the residue from hexane affords 247 mg. of S-ethyl 6,11-dihydrodibenzo-[b.e.]-thiepin-11-one-3-thioacetate, [(A), R =Et], m.p. 67° C.

EXAMPLE 3

A solution of 420 mg. of 6,11-dihydrodibenzo-[b.e.]-thiepin-11-one-3-acetic acid chloride in 15 ml. of dry methylene chloride is treated with 0.213 ml. of dry triethylamine and 0.165 ml. of α-toluenethiol. An immediate reaction occurs, as demonstrated by t.l.c. analysis. The reaction mixture is then diluted with 15 ml. of water and the product extracted with methylene chloride (2 ×20 ml.). The combined organic extract is washed with water (2 ×10 ml.), dried over anhydrous sodium sulfate and evaporated to dryness under reduced pressure. Purification of the oily residue by column chromatography on silica gel (8.4 g.), using hexane: ethyl acetate (85:15) as eluant affords 215 mg. of S-benzyl 6,11-dihydrodibenzo[b.e.]-thiepin-11-one-3-thioacetate, [(A), R = benzyl], an oil, having the following physical constants: U.V. $\lambda_{max}^{Diox}$ 248, 351 nm (ε 24500, 2750); I.R.: $\nu_{max}^{CHCl_3}$ 1715, 1650, 1600 cm$^{-1}$; N.M.R.: $\delta_{TMS}^{CDCL_3}$ 3.68 (s, 2H), 3.91 (s, 2H), 4.00 (s, 2H), 6.9–7.5 (m,11H), 7.99 (d, 1H).

EXAMPLE 4

A solution of 716 mg. or 6,11-dihydrodibenzo-[b.e.]-thiepin-11-one-3-acetic acid chloride in 20 ml. of dry methylene chloride is treated with 0.363 ml. of triethylamine and 0.267 ml. of thiophenol. An immediate reaction occurs, as demonstrated by t.l.c. analysis. The reaction mixture is diluted with 20 ml. of water and the product extracted with methylene chloride (2 × 40 ml.). The combined organic extract is washed with water (2 × 20 ml.), dried over anhydrous sodium sulfate and evaporated to dryness under reduced pressure. Purification of the residue by column chromatography on silica gel (14.3 g.) using hexane:ethyl acetate (85:15) as eluant, gives rise to 400 mg. of S-phenyl 6,11-dihydrodibenzo[b.e.]-thiepin-11-one-3-thioacetate [(A), R = phenyl], m.p. 97° C.

EXAMPLE 5

A solution of 316 mg. of (dl) 2-(6,11-dihydrodibenzo-[b.e.]-thiepin-11-one-3-yl) propionic acid chloride (I, R$^1$ =Me), in 15 ml. of dry methylene chloride is treated with 0.083 ml. of methyl mercaptan. The reaction mixture is kept at room temperature for 18 hours, 10 ml. of water are then added and the product extracted with methylene chloride (2 × 30 ml.). The combined organic extract is washed with water (2 × 15 ml.), dried over anhydrous sodium sulfate and evaporated to dryness under reduced pressure. Purification of the oily residue by column chromatography on silica gel (6.5 g.), using hexane:ethyl acetate (85:15) as eluant followed by crystallization from methylene chloride-hexane affords 239 mg. of S-methyl (dl) 2-(6,11-dihydrodibenzo-[b.e.]-thiepin-11-one-3-yl) thiopropionate [(B), R = Me], an oil, having the following physical constants: U.V.: $\lambda_{max}^{Diox}$ 252, 354 nm (ε 20900, 3020); I.R.: $\nu_{max}^{film}$ 1690, 1650, 1600 cm$^{-1}$, N.M.R.: $\delta_{TMS}^{CDCl_3}$ 1.43 (d, 3H), 2.20 (s, 3H), 3.80 (q, 1H) 3.95 (s, 2H), 6.8–7.5 (m, 6H), 8.03 (d, 1H).

In a similar manner by substituting the acid chloride derived from (d) 2-(6,11-dihydrodibenzo-[b.e.]-thiepin-11-one-3-yl) propionic acid for the (dl) mixture there is obtained S-methyl (d) 2-(6,11-dihydrodibenzo-[b.e.]-thiepin-11-one-3-yl) thiopropionate.

EXAMPLE 6

A solution of 316 mg. of (dl) 2-(6,11-dihydrodibenzo-[b.e.]-thiepin-11-one-3-yl) propionic acid chloride in 15 ml. of dry methylene chloride is treated with 0.110 ml. of ethyl mercaptan. The reaction mixture is kept at room temperature for 24 hours, 15 ml. of water are then added and the product extracted with methylene chloride (2 × +ml.). the combined organic extract is washed with water (2 × 15 ml.), dried over anhydrous sodium sulfate and evaporated to dryness under reduced pressure. Purification of the oily residue by column chromatography on silica gel (6.5 g.), using hexane:ethyl acetate (85:15) as eluant affords 270 mg. of S-ethyl (dl) 2-(6,11-dihydrodibenzo-[b.e.]-thiepin-11-one-3-yl) thiopropionate [(B), R = Et], an oil, having the following physical constants: U.V.: $\lambda_{max}^{Diox}$ 248, 350 nm (ε 25100, 3550); I.R.: $\nu_{max}^{film}$ 1685, 1650, 1600 cm$^{-1}$; N.M.R.: $\delta_{TMS}^{CDCl_3}$ 1.15 (t, 3H), 1.40 (t, 3H), 2.80 (q, 2H), 3.6–4.0 (b.m., 1H), 3.98 (s, 2H), 6.80–7.60 (m, 6H), 8.02 (d, 1H); M.S.: 342 (M+).

Likewise, substituting the acid chloride derived from (d) 2-(6,11-dihydrodibenzo-[b.e.]-thiepin-11-one-3-yl) propionic acid for the (dl) mixture there is obtained S-ethyl (d) 2-(6,11-dihydrodibenzo-[b.e.]-thiepin-11-one-3-yl) thiopropionate.

EXAMPLE 7

A solution of 0.3 g. of 6,11-dihydrodibenzo-[b.e.]-thiepin-11-one-3-acetic acid chloride in 20 of dry methylene chloride is stirred with 0.114 ml. of n-butyl mercaptan and 0.152 ml. of triethylamine. The reaction mixture is kept at room temperature for 15 minutes, and then evaporated to dryness in a current of nitrogen. The residue is chromatographed on 20 g. of silica gel, eluting with hexane:ethyl acetate (9:1). Evaporation of the eluate yields 160 mg. of S-n-butyl 6,11-dihydrodibenzo-[b.e.]-thiepin-11-one-3-thioacetate [(A), R = n-Bu], a pale yellow oil, having the following physical constants: U.V.: $\lambda_{max}^{Diox}$ 247, 280, 350 nm; (ε 27500, 9300, 3100); I.R.: $\nu_{max}^{CHCl_3}$ 1690, 1650 cm$^{-1}$; N.M.R.: $\delta_{TMS}^{CDCl_3}$ 0.84 (b.t, 3H), 1.00–1.80 (b.m, 4H), 2.81 (t, 2H), 3.70 (s, 2H), 3.95 (s, 2H), 6.90–7.60 (m, 6H), 8.07 ppm. (d, 1H).

EXAMPLE 8

A solution of 300 mg. of (dl) 2-(6,11-dihydrodibenzo-[b.e.]-thiepin-11-one-3-yl) propionic acid chloride in 20 ml. of methylene chloride is treated with stirring with 0.11 ml. of n-butyl mercaptan and 0.146 ml. of triethylamine. After 10 minutes the solvent is evaporated in a current of nitrogen and the residue is chromatographed on 20 g. of alumina, eluting with hexane:ethyl acetate (9:1). Evaporation of the eluate yields 330 mg. of S-n-butyl (dl) 2-(6,11-dihydrodibenzo-[b.e.]thiepin-11-one-3-yl) thiopropionate [(B), R = n-Bu), a pale yellow oil, which has the following physical constants: U.V.: $\lambda_{max}^{Diox}$ 249, 283, 354 nm; (ε 25100, 10000, 3020); I.R.: $\nu_{max}^{CHCl_3}$ 1690, 1650 cm$^{-1}$; N.M.R.: $\delta_{TMS}^{CDCl_3}$ 0.82 (b.t, 3H), 1.10–1.70 (m, 4H), 1.44 (d, 3H), 2.78 (t, 2H), 3.78 (q, 1H), 4.00 (s, 2H), 7.00–7.60 (m, 6H), 8.03 ppm. (d, 1H).

Likewise, substituting the acid chloride derived from (d) 2-(6,11-dihydrodibenzo-[b.e.]-thiepin-11-one-3-yl) propionic acid for the (dl) mixture, there is obtained S-n-butyl (d) 2-(6,11-dihydrodibenzo[b.e.]-thiepin-11-one-3-yl) thiopropionate.

EXAMPLE 9

A solution of 300 mg. of 6,11-dihydrodibenzo-[b.e.]-thiepin-11-one-3-acetic acid chloride in 20 ml. of dry methylene chloride is stirred with 0.151 ml. of n-hexyl mercaptan and 0.152 ml. of triethylamine. After 10 minutes the solvent is evaporated in a stream of nitrogen and the residue is chromatographed on 10 g. of silica gel, eluting with hexane:ethyl acetate (9:1). Evaporation of the eluate yields 165 mg. of S-n-hexyl 6,11-dihydrodibenzo-[b.e.]-thiepin-11-one-3-thioacetate, [(A), R = n-$C_6H_{13}$], a pale yellow oil having the following physical constants: U.V.: $\lambda_{max}^{Diox}$ 249, 282, 350 nm ($\epsilon$ 24500, 8700, 3000); I.R.: $\nu_{max}^{CHCl_3}$ 1690, 1650 cm$^{-1}$; N.M.R.: $\delta_{TMS}^{CDCl_3}$ 0.78 (b.t, 3H), 1.00–1.65 (m, 8H), 2.80 (t, 2H), 3.69 (s, 2H), 3.98 (s, 2H), 6.90–7.58 (m, 6H), 8.02 ppm. (d, 1H).

EXAMPLE 10

A solution of 300 mg. of (dl) 2-(6,11-dihydrodibenzo-[b.e.]-thiepin-11-one-3-yl) propionic acid chloride in 20 ml. of dry methylene chloride is stirred at room temperature with 0.145 ml. of n-hexyl mercaptan and 0.146 ml. of triethylamine for 10 minutes. The solvent is blown off in a stream of nitrogen and the residue is chromatographed on 10 g. of silica gel, eluting with hexane:ethyl acetate (9:1). Evaporation of the eluate yields S-n-hexyl (dl) 2-(6,11-dihydrodibenzo-[b.e.]-thiepin-11-one-3-yl) thiopropionate [(B), R = n-$C_6H_{13}$], as a pale yellow oil, having the following physical constants: U.V.: $\epsilon_{max}^{D10x}$ 250, 283, 350 nm; 24900, 8600, 3100); I.R.: $\lambda_{max}^{CHCl_3}$ 1690, 1650 cm$^{-1}$; N.M.R.: $\delta_{TMS}^{CDCl_3}$ 0.78 (b.t, 3H), 1.00–1.70 (m, 8H), 1.46 (d, 3H), 2.74 (t, 2H), 3.74 (q, 1H), 3.94 (s, 2H), 6.94–7.60 (m, 6H), 8.03 ppm. (d, 1H).

Similarly, substituting the acid chloride derived from (d) 2-(6,11-dihydrodibenzo:[b.e.]-thiepin-11-one-3-yl) propionic acid for the (dl) mixture, there is obtained S-n-hexyl (d) 2-(6,11-dihydrodibenzo-[b.e.]-thiepin-11-one-3-yl) thiopropionate.

EXAMPLE 11

A. To 120 ml. of methylene chloride, cooled to 0° C there are added 2.5 g. of 6,11-dihydrodibenzo-[b.e.]-thiepin-11-one-3-aldehyde (II), 13 g. of triphenylphosphine and 10 g. of carbon tetrabromide, under a nitrogen atmosphere. The reaction mixture is kept at 0° C for 1 hour, and then filtered through Celite (diatomaceous earth). The filtrate is evaporated to dryness and the residue is chromatographed through a column of 150 g. of Florisil, eluting with hexane: methylene chloride (7:3). Evaporation of the eluate yields a crystalline solid which is recrystallized from methylene chloride-methanol, to yield 3.36 g. of 3-(2,2-dibromo) vinyl-6,11-dihydrodibenzo-[b.e.]-thiepin-11-one (III), m.p. 124° C.

B. A solution of 1.0 g. of methyl mercaptan in 5 ml. of dimethylformamide is slowly addded, with stirring, to a suspension of 150 mg. of sodium hydride in 20 ml. of dimethylformamide. The temperature of the reaction mixture is maintained at about 0° C with ice cooling. When all the sodium hydride is dissolved, a solution of 800 mg. of 3-(2,2-dibromo) vinyl-6,11-dihydrodibenzo-[b.e.]-thiepin-11-one in 10 ml. of dimethylformamide is added all at once. The reaction mixture is stirred for 30 minutes at 0° C and then for 1 hour at room temperature. The reaction is quenched by pouring into 200 ml. of water and the product extracted with ethyl acetate (3 × 50 ml.). The combined extracts are dried over sodium sulfate and evaporated. The residue is filtered through 25 g. of silica gel, eluting with hexane-ethyl acetate (9:1). Evaporation of the eluate yields 659 mg. of 3-[2,2-bis (thiomethyl)] vinyl-6,11-dihydrodibenzo-[b.e.]-thiepin-11-one (IV), an oil, having the following physical constants: U.V.: $\lambda_{max}^{MeOH}$ 250, 354 nm ($\epsilon$ 20400, 18600); I.R.: $\nu_{max}^{CHCl_3}$ 1650, 1370 cm$^{-1}$; N.M.R.: $\delta_{TMS}^{CDCl_3}$ 2.29–2.31 (2 × s, 6H), 3.95 (s, 2H), 6.42 (s, 1H), 7.0–7.6 (m, 6H), 8.10 ppm. (d, 1H); M.S.: m/e 344 (M+).

C. A mixture of 100 of 3-[2,2-bis (thiomethyl)] vinyl-6,11-dihydrodibenzo-[b.e.]-thiepin-11-one and 300 mg. of trifluoroacetic acid is stirred at room temperature for 20 minutes, 54 mg. of water is added and the stirring is continued for a further 18 hours. The reaction is quenched with 10 ml. of water and the product is extracted with ethyl acetate. The combined extracts are washed with aqueous 10% sodium bicarbonate solution and water, dried over anhydrous sodium sulfate and evaporated. Crystallization of the residue from methylene chloride-hexane affords 64 mg. of S-methyl-6,11-dihydrodibenzo-[b.e.]-thiepin-11-one-3-thioacetate [(A), R = Me], m.p. 95°–96° C, identical to the product obtained in Example 1.

EXAMPLE 12

Example 3 is repeated using stoichiometric equivalent amounts of the substituted benzyl mercaptans listed below under I in place of α-toluenethiol, to produce the corresponding thioesters listed under II.

| I | II |
|---|---|
| m-methoxybenzyl mercaptan | S-(m-methoxybenzyl)-6,11-dihydrodibenzo-[b.e.]-thiepin-11-one-3-thioacetate. |
| o-methylbenzyl mercaptan | S-(o-methylbenzyl)-6,11-dihydrodibenzo-[b.e.]-thiepin-11-one-3-thioacetate. |
| p-ethylbenzyl mercaptan | S-(p-ethylbenzyl)-6,11-dihydrodibenzo-[b.e.]-thiepin-11-one-3-thioacetate. |
| o-isopropoxybenzyl mercaptan | S-(p-isopropoxybenzyl)-6,11-dihydrodibenzo-[b.e.]-thiepin-11-one-3-thioacetate. |
| p-ethoxybenzyl mercaptan | S-(p-ethoxybenzyl)-6,11-dihydrodibenzo-[b.e.]-thiepin-11-one-3-thioacetate. |
| o-chlorobenzyl mercaptan | S-(o-chlorobenzyl)-6,11-dihydrodibenzo-[b.e.]-thiepin-11-one-3-thioacetate. |
| m-chlorobenzyl mercaptan | S-(m-chlorobenzyl)-6,11-dihydrodibenzo-[b.e.]-thiepin-11-one-3-thioacetate. |
| m-bromobenzyl mercaptan | S-(m-bromobenzyl)-6,11-dihydrodibenzo-[b.e.]-thiepin-11-one-3-thioacetate. |
| p-bromobenzyl mercaptan | S-(p-bromobenzyl)-6,11-dihydrodibenzo-[b.e.]-thiepin-11-one-3-thioacetate. |
| o-fluorobenzyl mercaptan | S-(o-fluorobenzyl)-6,11-dihydrodibenzo-[b.e.]-thiepin-11-one-3-thioacetate. |
| p-fluorobenzyl mercaptan | S-(p-fluorobenzyl)-6,11-dihydrodibenzo-[b.e.]-thiepin-11-one-3-thioacetate. |

EXAMPLE 13

Example 4 is repeated using stoichiometric equivalent amounts of the substituted thiophenols listed below under I in place of thiophenol, to produce the corresponding thioesters listed under II.

| I | II |
|---|---|
| o-thiocresol | S-(o-tolyl)-6,11-dihydrodibenzo-[b.e.]-thiepin-11-one-3-thioacetate. |
| p-thiocresol | S-(p-tolyl)-6,11-dihydrodibenzo-[b.e.]-thiepin-11-one-3-thioacetate. |
| o-ethylthiophenol | S-(o-ethylphenyl)-6,11-dihydrodibenzo-[b.e.]-thiepin-11-one-3-thioacetate. |
| o-t-butylthiophenol | S-(o-t-butylphenyl)-6,11-dihydrodibenzo-[b.e.]-thiepin-11-one-3-thioacetate. |

-continued

| I | II |
|---|---|
| m-sec-butylthiophenol | S-(m-sec-butylphenyl)-6,11-dihydrodibenzo-[b.e.]-thiepin-11-one-3-thioacetate. |
| p-methoxythiophenol | S-(p-methoxyphenyl)-6,11-dihydrodibenzo-[b.e.]-thiepin-11-one-3-thioacetate. |
| p-ethoxythiophenol | S-(p-ethoxyphenyl)-6,11-dihydrodibenzo-[b.e.]-thiepin-11-one-3-thioacetate. |
| o-bromothiophenol | S-(o-bromophenyl)-6,11-dihydrodibenzo-[b.e.]-thiepin-11-one-3-thioacetate. |
| p-bromothiophenol | S-(p-bromophenyl)-6,11-dihydrodibenzo-[b.e.]-thiepin-11-one-3-thioacetate. |
| m-chlorothiophenol | S-(m-chlorophenyl)-6,11-dihydrodibenzo-[b.e.]-thiepin-11-one-3-thioacetate. |
| p-chlorothiophenol | S-(p-chlorophenyl)-6,11-dihydrodibenzo-[b.e.]-thiepin-11-one-3-thioacetate. |
| o-fluorothiophenol | S-(o-fluorophenyl)-6,11-dihydrodibenzo-[b.e.]-thiepin-11-one-3-thioacetate. |
| p-fluorothiophenol | S-(p-fluorophenyl)-6,11-dihydrodibenzo-[b.e.]-thiepin-11-one-3-thioacetate. |

EXAMPLE 14

By following the method of Example 3 (dl) 2-(6,11-dihydrodibenzo-[b.e.]-thiepin-11-one-3-yl) propionic acid chloride is treated with α-toluenethiol, to produce S-benzyl (dl) 2-(6,11-dihydrodibenzo-[b.e.]-thiepin-11-one-3-yl) thiopropionate.

Similarly using the individual acid chloride isomer derived from the (d) acid in place of the (dl) mixture there is obtained S-benzyl (d) 2-(6,11-dihydrodibenzo-[b.e.]-thiepin-11-one-3-yl) thiopropionate.

By the same method but using the substituted benzyl mercaptans listed in Example 12 in place of α-toluenethiol, there are respectively obtained:

S-(m-methoxybenzyl) (dl) 2-(6,11-dihydrodibenzo-[b.e.]-thiepin-11-one-3-yl) thiopropionate,
S-(o-methylbenzyl) (dl) 2-(6,11-dihydrodibenzo-[b.e.]-thiepin-11-one-3-yl) thiopropionate,
S-(p-ethylbenzyl) (dl) 2-(6,11-dihydrodibenzo-[b.e.]-thiepin-11-one-3-yl) thiopropionate,
S-(o-isopropoxybenzyl) (dl) 2-(6,11-dihydrodibenzo-[b.e.]-thiepin-11-one-3-yl) thiopropionate,
S-(p-ethoxybenzyl) (dl) 2-(6,11-dihydrodibenzo-[b.e.]-thiepin-11-one-3-yl) thiopropionate,
S-(o-chlorobenzyl) (dl) 2-(6,11-dihydrodibenzo-[b.e.]-thiepin-11-one-3-yl) thiopropionate,
S-(m-chlorobenzyl) (dl) 2-(6,11-dihydrodibenzo-[b.e.]-thiepin-11-one-3-yl) thiopropionate,
S-(m-bromobenzyl) (dl) 2-(6,11-dihydrodibenzo-[b.e.]-thiepin-11-one-3-yl) thiopropionate,
S-(p-bromobenzyl) (dl) 2-(6,11-dihydrodibenzo-[b.e.]-thiepin-11-one-3-yl) thiopropionate,
S-(o-fluorobenzyl) (dl) 2-(6,11-dihydrodibenzo-[b.e.]-thiepin-11-one-3-yl) thiopropionate,
S-(p-fluorobenzyl) (dl) 2-(6,11-dihydrodibenzo-[b.e.]-thiepin-11-one-3-yl) thiopropionate, as well as the corresponding thioesters of the individual (d) isomers.

EXAMPLE 15

Example 4 is repeated using (dl) 2-(6,11-dihydrodibenzo-[b.e.]-thiepin-11-one-3-yl) propionic acid chloride as starting material, thus obtaining S-phenyl (dl) 2-(6,11-dihydrodibenzo-[b.e.]-thiepin-11-one-3-yl) thiopropionate.

Similarly, using the individual acid chloride isomer derived from the (d) acid in place of the (dl) mixture there is obtained S-phenyl (d) 2-(6,11-dihydrodibenzo-[b.e.]-thiepin-11-one-3-yl) thiopropionate.

By the same method but using the substituted thiophenols listed in Example 13 in place of thiophenol there are respectively obtained:

S-(o-tolyl) (dl) 2-(6,11-dihydrodibenzo-[b.e.]-thiepin-11-one-3-yl) thiopropionate,
S-(p-tolyl) (dl) 2-(6,11-dihydrodibenzo-[b.e.]-thiepin-11-one-3-yl) thiopropionate,
S-(o-ethylphenyl) (dl) 2-(6,11-dihydrodibenzo-[b.e.]-thiepin-11-one-3-yl) thiopropionate,
S-(o-t-butylphenyl) (dl) 2-(6,11-dihydrodibenzo-[b.e.]-thiepin-11-one-3-yl) thiopropionate,
S-(m-sec-butylphenyl) (dl) 2-(6,11-dihydrodibenzo-[b.e.]-thiepin-11-one-3-yl) thiopropionate,
S-(p-methoxyphenyl) (dl) 2-(6,11-dihydrodibenzo-[b.e.]-thiepin-11-one-3-yl) thiopropionate,
S-(p-ethoxyphenyl) (dl) 2-(6,11-dihydrodibenzo-[b.e.]-thiepin-11-one-3-yl) thiopropionate,
S-(o-bromophenyl) (dl) 2-(6,11-dihydrdibenzo-[b.e.]-thiepin-11-one-3-yl) thiopropionate,
S-(p-bromophenyl) 2-(6,11-dihydrodibenzo-[b.e.]-thiepin-11-one-3-yl) thiopropionate,
S-(m-chlorophenyl) (dl) 2-(6,11-dihydrodibenzo-[b.e.]-thiepin-11-one-3-yl) thiopropionate,
S-(p-chlorophenyl) (dl) 2-(6,11-dihydrodibenzo-[b.e.]-thiepin-11-one-3-yl) thiopropionate,
S-(o-fluorophenyl) (dl) 2-(6,11-dihydrodibenzo-[b.e.]-thiepin-11-one-2-yl) thiopropionate and
S-(p-fluorophenyl) (dl) 2-(6,11-dihydrodibenzo-[b.e.]-thiepin-11-one-3-yl) thiopropionate, as well as the corresponding thioesters of the individual (d) acid isomers.

What is claimed is:

1. A compound selected from the group of those represented by the formulas

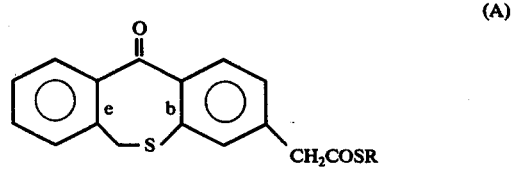

(A)

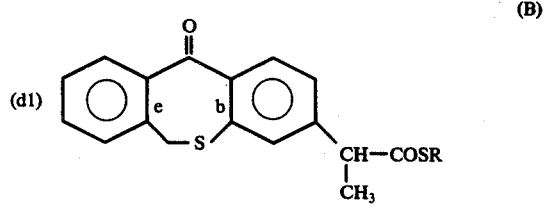

(B)

or the individual (d) isomers of the compounds of Formula (B), wherein R is a lower alkyl group of one to six carbon atoms, phenyl, monosubstituted phenyl, benzyl or monosubstituted benzyl, said substitution in the phenyl and benzyl groups consisting of alkyl of 1 to 4 carbon atoms, alkoxy of 1 to 4 carbon atoms, chloro, bromo or fluoro, at the o-, m- or p-positions of the aromatic ring.

2. A compound of claim 1 wherein R is lower alkyl.

3. A compound of claim 1 wherein R is phenyl or substituted phenyl.

4. A compound of claim 1 wherein R is benzyl or substituted benzyl.

5. The compound of claim 2 Formula (A) wherein R is methyl, S-methyl 6,11-dihydrodibenzo-[b.e.]-thiepin-11-one-3-thioacetate.

6. The compound of claim 2 Formula (A) wherein R is ethyl, S-ethyl 6,11-dihydrodibenzo-[b.e.]-thiepin-11-one-3-thioacetate.

7. The compound of claim 2 Formula (A) wherein R is n-butyl, S-n-butyl 6,11-dihydrodibenzo[b.e.]-thiepin-11-one-3-thioacetate.

8. The compound of claim 2 Formula (A) wherein R is n-hexyl, S-n-hexyl 6,11-dihydrobenzo-[b.e.]-thiepin-11-one-3-thioacetate.

9. The compound of claim 3 Formula (A) wherein R is phenyl, S-phenyl 6,11-dihydrodibenzo-[b.e.]-thiepin-11-one-3-thioacetate.

10. The compound of claim 4 Formula (A) wherein R is benzyl, S-benzyl 6,11-dihydrodibenzo-[b.e.]-thiepin-11-one-3-thioacetate.

11. The (dl) compound of claim 2, Formula (B), wherein R is methyl, S-methyl (dl) 2-(6,11-dihydrodibenzo-[b.e.]-thiepin-11-one-3-yl)thiopropionate.

12. The (dl) compound of claim 2, Formula (B), wherein R is ethyl, S-ethyl (dl) 2-(6,11-dihydrodibenzo-[b.e.]-thiepin-11-one-3-yl)thiopropionate.

13. The (dl) compound of claim 2, Formula (B), wherein R is n-butyl, S-n-butyl (dl) 2-(6,11-dihydrodibenzo-[b.e.]-thiepin-11-one-3-yl)thiopropionate.

14. The (dl) compound of claim 2, Formula (B), wherein R is n-hexyl, S-n-hexyl (dl) 2-(6,11-dihydrodibenzo-[b.e.]-thiepin-11-one-3-yl)thiopropionate.

15. The (dl) compound of claim 2, Formula (B), wherein R is phenyl, S-phenyl (dl) 2-(6,11-dihydrodibenzo-[b.e.]-thiepin-11-one-3-yl)thiopropionate.

16. The (dl) compound of claim 2, Formula(B), wherein R is benzyl, S-benzyl (dl) 2-(6,11-dihydrodibenzo-[b.e.]-thiepin-11-one-3-yl)thiopropionate.

17. A compound of the formula

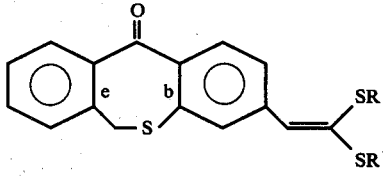

wherein R is a lower alkyl group of one to six carbon atoms, phenyl, monosubstituted phenyl, benzyl, or monosubstituted benzyl, said substitution in the phenyl and benzyl groups consisting of alkyl of 1 to 4 carbon atoms, alkoxy of 1 to 4 carbon atoms, chloro, bromo or fluoro, at the o-, m- or p-positions of the aromatic ring.

18. The compound of claim 17 wherein R is methyl, 3-[2,2-bis(thiomethyl)]vinyl-6,11-dihydrodibenzo-[b.e.]-thiepin-11-one.

* * * * *